(12) United States Patent
Rönnback et al.

(10) Patent No.: US 12,263,246 B2
(45) Date of Patent: Apr. 1, 2025

(54) MANUFACTURING OF PHARMACEUTICAL COMPOSITIONS

(71) Applicant: FERRING INTERNATIONAL CENTER S.A., Saint-Prex (CH)

(72) Inventors: Robert Rönnback, Morges (CH); Josselin Saunier, La Tour-de-Peilz (CH)

(73) Assignee: FERRING INTERNATIONAL CENTER S.A., Saint-Prex (CH)

( * ) Notice: Subject to any disclaimer, the term of this patent is extended or adjusted under 35 U.S.C. 154(b) by 1323 days.

(21) Appl. No.: 16/648,372

(22) PCT Filed: Sep. 17, 2018

(86) PCT No.: PCT/EP2018/075034
§ 371 (c)(1),
(2) Date: Mar. 18, 2020

(87) PCT Pub. No.: WO2019/053247
PCT Pub. Date: Mar. 21, 2019

(65) Prior Publication Data
US 2020/0222319 A1    Jul. 16, 2020

(30) Foreign Application Priority Data

Sep. 18, 2017 (EP) ..................................... 17191652

(51) Int. Cl.
*B01F 33/82*    (2022.01)
*A61K 9/08*     (2006.01)
(Continued)

(52) U.S. Cl.
CPC .............. *A61K 9/08* (2013.01); *B01F 23/024* (2022.01); *B01F 27/1143* (2022.01);
(Continued)

(58) Field of Classification Search
CPC .......................... B01F 33/821; B01F 35/2203
(Continued)

(56) References Cited

U.S. PATENT DOCUMENTS 3,034,046 A * 5/1962 Sasaki ..................... G05D 22/02
                                                                34/259
3,644,826 A * 2/1972 Cornetet, Jr. .......... G01N 22/04
                                                                250/359.1
(Continued)

FOREIGN PATENT DOCUMENTS

| CN | 1251662 C | 4/2006 |
| CN | 102014846 A | 4/2011 |

(Continued)

OTHER PUBLICATIONS

Office Action issued on Nov. 18, 2021, in Chinese Application No. 201880074151.8.
(Continued)

*Primary Examiner* — David L Sorkin
(74) *Attorney, Agent, or Firm* — Foley & Lardner LLP

(57) ABSTRACT

The present disclosure discloses a process for the continuous manufacture of a liquid pharmaceutical composition, the process comprising providing a mixing unit, feeding a therapeutic agent and a liquid vehicle to the mixing unit, operating the latter thereby mixing the agent and the vehicle into a liquid pharmaceutical composition, discharging the composition into a holding unit.

5 Claims, 1 Drawing Sheet

(51) Int. Cl.
    *B01F 23/00* (2022.01)
    *B01F 27/1143* (2022.01)
    *B01F 33/84* (2022.01)
    *B01F 35/21* (2022.01)
    *B01F 35/214* (2022.01)
    *B01F 35/22* (2022.01)
    *B01F 35/82* (2022.01)
    *B01F 101/22* (2022.01)

(52) U.S. Cl.
    CPC ............ *B01F 33/821* (2022.01); *B01F 33/84* (2022.01); *B01F 35/21111* (2022.01); *B01F 35/2132* (2022.01); *B01F 35/2144* (2022.01); *B01F 35/2203* (2022.01); *B01F 35/82* (2022.01); *B01F 23/062* (2022.01); *B01F 35/2117* (2022.01); *B01F 35/2135* (2022.01); *B01F 2101/22* (2022.01)

(58) Field of Classification Search
    USPC .............................................. 366/141, 152.1
    See application file for complete search history.

(56) References Cited

U.S. PATENT DOCUMENTS

| | | | |
|---|---|---|---|
| 5,302,394 A | 4/1994 | Beahm | |
| 5,350,234 A | 9/1994 | Hagen | |
| 6,254,269 B1 | 7/2001 | Ernstson et al. | |
| 8,916,219 B2 * | 12/2014 | Philipp | A23G 3/0044 |
| | | | 426/660 |
| 8,960,997 B2 * | 2/2015 | Bachman | A01K 5/001 |
| | | | 119/51.01 |
| 2005/0270899 A1 | 12/2005 | Phallen et al. | |
| 2008/0279038 A1 | 11/2008 | Bellafiore et al. | |
| 2011/0037185 A1 | 2/2011 | Kowalski et al. | |
| 2012/0241045 A1 | 9/2012 | Aouad | |

FOREIGN PATENT DOCUMENTS

| | | |
|---|---|---|
| CN | 202777089 U | 3/2013 |
| CN | 105075457 A | 11/2015 |
| CN | 105686032 A | 6/2016 |
| EP | 0 918 562 B1 | 3/2003 |
| EP | 1 778 194 B1 | 4/2015 |
| JP | H10-337459 A | 12/1998 |
| KR | 1020000016272 A | 3/2000 |
| WO | WO-97/46308 A1 | 12/1997 |
| WO | WO-2006/010921 A1 | 2/2006 |
| WO | WO-2017/129988 A1 | 8/2017 |
| WO | WO-2017/155669 A1 | 9/2017 |

OTHER PUBLICATIONS

Office Action issued on Jul. 8, 2022, in Brazilian Application No. BR112020004952-2.

Office Action received in Japanese Application No. 2020-515736 dated Jan. 20, 2023.

Office Action (Notice of Reasons for Rejection) dated Aug. 23, 2022 in JP 2020-515736.

Office Action issued on Feb. 9, 2021, in Eurasian Application No. 202090508.

Office Action received in Korean Application No. 10-2020-7010134 dated Jan. 1, 2023.

* cited by examiner

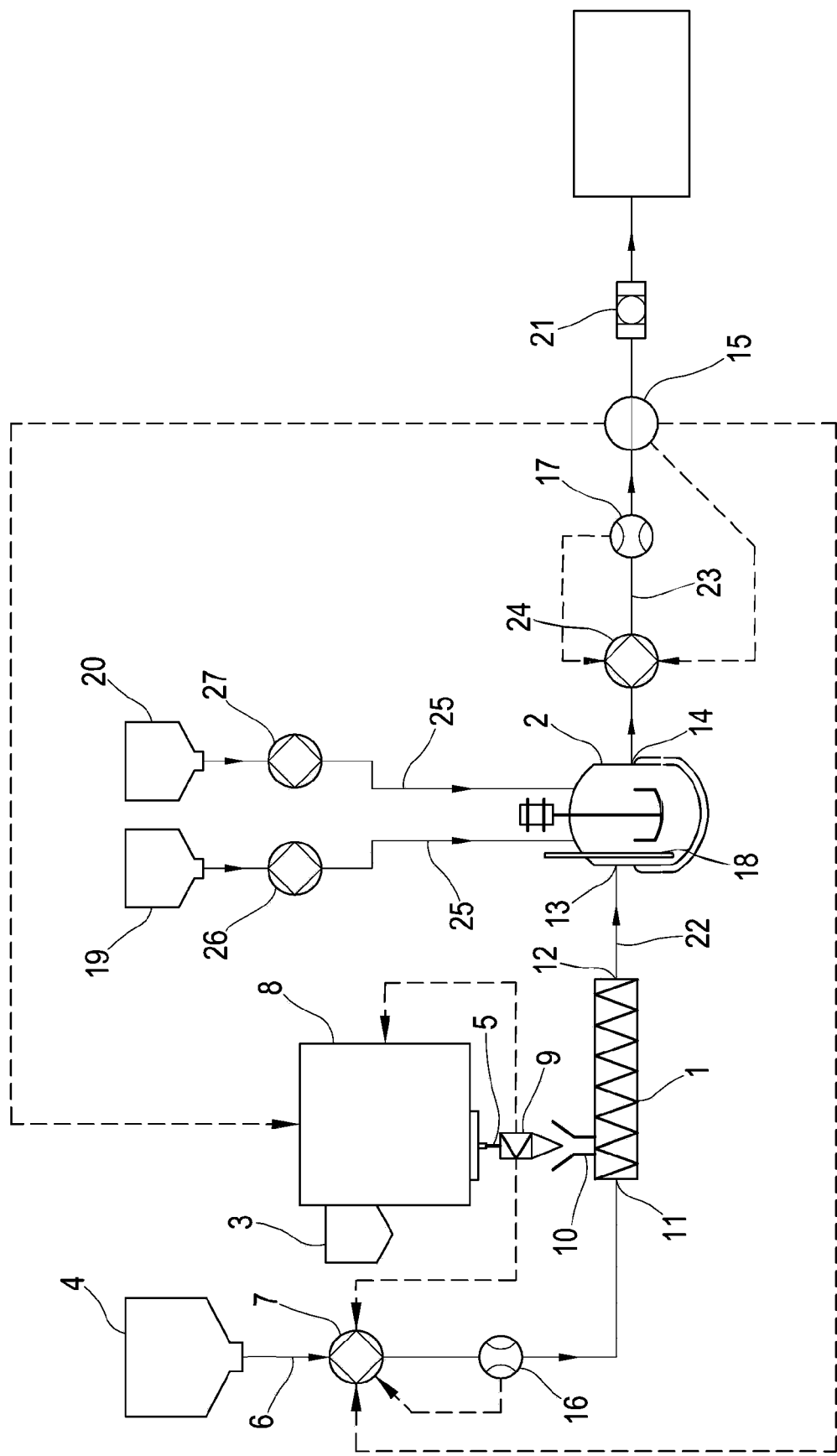

MANUFACTURING OF PHARMACEUTICAL COMPOSITIONS

CROSS-REFERENCE TO RELATED APPLICATIONS

The present application is the U.S. National Stage of International Application No. PCT/EP2018/075034, filed Sep. 17, 2018, and claims priority to European Patent Application No. 17191652.1, filed Sep. 18, 2017.

BACKGROUND

The present disclosure relates to an continuous manufacturing process for liquid pharmaceutical compositions, in particular compositions containing biotechnological drugs, as well as an apparatus suitable to carry out that process. Several medicinal products are administered to patients in the form of liquid compositions or compositions obtainable by further processing liquid compositions (e.g. freeze-dried compositions). These compositions are typically obtained through manufacturing processes that include a step in which a therapeutic agent (hereinafter also referred to as "API" or "active ingredient") is admixed with a liquid vehicle so as to obtain a predetermined API concentration.

BRIEF DESCRIPTION OF THE FIGURES

FIG. 1 is a block diagram disclosing a schematic illustration of the functional relationship of piping, instrumentation and system equipment components of an embodiment of the process presently disclosed wherein the process is run on a continuous basis. In the FIGURE, the continuous lines identify the piping elements through which materials flow. Dashed lines identify the existence of typically computer controlled systems wherein data drawn from a downstream instrument/component are used to control the functioning of an upstream instrument/component (according to the flow direction indicated in the FIGURE).

DETAILED DESCRIPTION

An object of the present disclosure is to provide an continuous manufacturing process for liquid pharmaceutical compositions that ensures inter alia an appropriate in-line (real-time) control over product characteristics, notably API concentration. This is important in order to obtain a composition (and dosage form units containing the same) with precise and accurate API content over time. Irrespective of the intrinsic properties of a given therapeutic agent, ensuring appropriate content uniformity may be particularly challenging in case of low nominal API concentrations, such as for high potent APIs (aka HPAPI) wherein even minor fluctuations in API concentration may have serious consequences.

Another object of the present disclosure is to provide a process as defined above, which targets a low overall residence time, i.e. wherein the time between the supply of a therapeutic agent from e.g. a bulk reservoir and the provision of the final composition is short. Achieving low residence time is considered to be advantageous for example for formulating labile APIs. Also, a process with low residence time generally has faster start-up and shutdown periods, which make it particularly attractive for R&D purposes or/and small volume manufacturing.

Another object of the present disclosure is to provide a process as defined above having a small footprint. Another object of the present disclosure is to provide a process as defined above with a reduced waste production and margin of error with respect to conventional processes.

Another object of the present disclosure is to provide an apparatus suitable to carry out a process as defined above, for example an apparatus having a small footprint. Ideally, the apparatus should be suitable for running the process both at lab scale and industrial scale wherein the scaling up of the process may be obtained by adjusting the run time rather then the apparatus footprint (e.g. apparatus units size).

These and other objects are solved by a process, an apparatus and the uses as defined in the appended claims.

Below, the various aspects of the present disclosure will be disclosed in greater detail. For the sake of conciseness, certain features will be discussed only in connection with one aspect. However, it shall be understood that these features are equally applicable to all other aspects to which they are technically relevant.

In a first aspect, the present disclosure discloses a process for the continuous manufacture of a liquid pharmaceutical composition, the process comprising the steps of:
  providing a supply of a therapeutic agent and a supply of a liquid vehicle,
  dispensing the therapeutic agent and the liquid vehicle from the corresponding supplies and feeding them into a mixing unit 1, said dispensing and feeding being performed according to a predetermined, timely-steady rate, the rate of the agent and the rate of the liquid vehicle being each independently adjustable,
  operating the mixing unit 1 thereby obtaining a liquid composition having a therapeutic agent concentration,
  discharging the liquid composition from the mixing unit 1 into a holding unit 2, the holding unit 2 being configured so that the unit residence time of the liquid composition is at least sufficient to normalize the therapeutic agent concentration,
  discharging the liquid composition from the holding unit 2 and processing the same.

Unless otherwise stated, "a" or "an" mean one or more.

Unless otherwise stated, states of matter—e.g. whether matter is liquid or solid—are assessed at standard ambient temperature and pressure, e.g. at about 25° C. and about 1 bar.

Unless otherwise stated, a composition is a "pharmaceutical composition" whenever it includes a therapeutic agent. A therapeutic agent is a substance known for, or simply presented for treating or preventing disease in human beings or animals and any substance which may be administered to human beings or animals with a view to making a medical diagnosis or to restoring, correcting or modifying physiological functions in humans or in animals. Combinations of therapeutic agents are possible. The therapeutic agent may include chemicals (also known as "small molecules") and/or biotechnological therapeutic agents such as peptides, proteins and antibodies. A typical biotechnological therapeutic agent is a peptide or a protein. The therapeutic agent may be in solid or liquid state. For example, it can be in the form of bulk powder or granules. When in solid form, therapeutic agents may be in crystalline or amorphous form. Therapeutic agents that would be liquid at ambient temperature and pressure may be dispensed in solid form if subjected to appropriate processing. In this case, the therapeutic agent may be preliminary frozen before being supplied to a dispensing unit.

With respect to a given liquid vehicle, suitable therapeutic agents may have any solubility. For example, agents may have a solubility defined as from "soluble" to "practically insoluble", or from "sparingly soluble" to "practically insoluble", such as from "slightly soluble" to "practically insoluble" or from "very slightly soluble" to "practically insoluble", according to USP 26, NF 21 2003. Solubility may be tested according to the protocol and using the apparatus as defined in Ph. Eur. 9th Ed. 5.11. Characters section in monographs.

Based on the solubility of the chosen active agent(s) in the chosen liquid vehicle, the present liquid composition may be in the form of a solution or a suspension. The further processing of the liquid composition may change its physical form when discharged from the holding unit and e.g. make it solid (e.g. by freeze-drying). This can be the case of compositions intended for reconstitution of extemporary suspensions.

If more than one therapeutic agent is used, each agent may have a distinct solubility in the chosen liquid vehicle, and/or a different physical form when supplied to the process.

The liquid vehicle typically contains pharmaceutically acceptable liquids such as water and/or other solvents, preferably water. Water may be any type of USP29 monograph purified water, for example water for pharmaceutical applications, distilled water or water for sterile injection. The liquid vehicle may include water in an amount of more than about 50%, for example 60% or 70% by weight over the weight of a unit sample of the vehicle. The liquid vehicle may essentially consist of water.

The liquid vehicle may further include pharmaceutically acceptable excipients typically used for the manufacture of liquid pharmaceutical formulations. For example, the vehicle may include an excipient selected from the group consisting of a buffering agent, an isotonicity agent (e.g. an osmotic agent), a solubilizing agent, a stabilizing agent, an antioxidant and mixtures thereof.

A qualitative example of a liquid vehicle is as follows:
An antioxidant, such as L-methionine,
A buffer agent, such as succinic acid,
An isotonicity agent such as mannitol,
A pH adjusting agent such as sodium hydroxide, and
Water, such as water for injection.

Another qualitative example of a liquid vehicle is as follows:
An isotonicity agent such as mannitol,
A pH adjusting agent such as hydrochloride acid, and
Water, such as water for injection.
All ingredients may be used as USP grade.

The presently disclosed process is suitable to obtain liquid pharmaceutical compositions that contain more than about 0.05 mg/mL, for example between about 0.1 mg/mL and about 7.5 mg/mL of a therapeutic agent per volume unit of the composition.

The process presently disclosed is run on a continuous basis, as opposed to the conventional batch manufacturing technique. Unless otherwise stated, the term "continuous process" includes both continuous and semi-continuous schemes, preferably it refers to continuous scheme. Characteristics of continuous and batch manufacturing schemes are known in the field of pharmaceuticals. For example, with respect to batch manufacturing, frequency of breaks between various process stages is absent in case of continuous manufacturing design. The process presently disclosed may be an automated one. Automation of the process line is advantageous as it reduces human interference and the margin of production errors.

Transforming a batch manufacturing process into a continuous one may be particularly challenging, especially for pharmaceuticals, in light of the tight quality and safety criteria to be met in this field. In case of manufacturing of liquid pharmaceutical compositions (or compositions obtained by processing liquid ones), one of the major challenges is represented by the need to normalize (and also possibly prevent) fluctuations—e.g. positive or negative peaks—in the concentration of the therapeutic agent over time. The present disclosure discloses a solution to obtain an effective and fully controlled manufacturing of a liquid pharmaceutical composition that avoids this problem while benefiting from the advantages that are typically associated with continuous manufacturing techniques. Although it is not intended to be bound by any theory, the achievement and maintenance of a predetermined, target concentration of the therapeutic agent in the composition is believed to be rooted in having designed a process core wherein a mixing unit is coupled downstream to a holding unit and also to the presence of other optional features convergingly acting on the prevention and normalization of fluctuations in the concentration of the therapeutic agent over time. Due to its characteristics, the present process is particularly suitable for formulating high potency active pharmaceutical ingredient (aka HPAPI), i.e. compounds that are typically used in very low amounts and for whom even minor fluctuations of the concentration may have important consequences on the composition safety and quality.

Process residence time (RT) is a known critical equipment and process parameter often used in manufacturing processes to characterize the period of time a solid or a fluid stays in, or flows through one or more process units in a continuous process. As used herein, the term "residence time" has its conventional meaning and refers to the length of time that the liquid composition stays or flows in a defined unit or a device, e.g. the residence time of the liquid composition in the mixing unit, or the residence time of the liquid composition in the holding unit. The overall residence time of the liquid composition is the combination of all partial, unit/device specific residence times. Unless otherwise stated, mentions of RT in the present disclosure refer to mean RT. The RT of a given unit is believed to depend on both unit volume and process parameters. In particular, although it is not intended to be bound by any theory, it is believed that unit volume influences the mean RT, whereas process parameters influence RT distribution (i.e. how RT varies around the mean value). In simpler words, the process parameters being equal, the RT of a given unit depends on material parameters influencing the unit volume, notably unit size. In case of the holding tank, whose geometry is relatively simple, unit size can be considered to equal its volume thereby being the main parameter determining the tank residence time of the liquid composition.

The supplies of the therapeutic agent and the liquid vehicle may be initially contained in dedicated dispensing units 3 and 4, such as reservoirs (e.g. a hopper for the therapeutic agent and a tank for the liquid vehicle) that are fluidly connected to the mixing unit 1 through conveying elements 5 and 6. Filling of the dispensing units 3 and 4 according to a known "top-up" technique allows running the process in continuous manner without halting the same when the supply is ended.

Once dispensed from the corresponding dispensing units 3 and 4, the supplies of the therapeutic agent and the liquid vehicle may be fed to, and admixed within the mixing unit 1. Alternatively, they may be admixed upstream, such as immediately upstream, to the mixing unit 1. To avoid possible stability problems, it is preferred that the therapeutic agent and the liquid vehicle do not get in contact before being fed to the mixing unit 1.

The dispensing and feeding of the therapeutic agent and the liquid vehicle from the corresponding supplies is performed continuously according to a predetermined, timely-steady rate. Unless otherwise stated, predetermined, timely-steady rate means that the amount (preferably expressed by weight) of the therapeutic agent and the amount (preferably expressed by volume) of the liquid vehicle that are dispensed from the corresponding supplies and fed into the mixing unit 1 correspond to values predetermined to achieve a desired qualitative and/or quantitative result, typically a target concentration, and remain steady per time unit (e.g. a minute or an hour).

The predetermined, timely-steady rate may be obtained by dispensing and feeding the agent and the vehicle as a steady flow. For the therapeutic agent, the predetermined, timely-steady rate may alternatively be obtained by dispensing and feeding the same in physically discrete sub-amounts, i.e. according to a frequency. Frequency parameters may vary over time provided that the resulting rate remains as predetermined and timely-steady.

The rate of the therapeutic agent and the rate of the liquid vehicle are each independently adjustable. This means that the process presently disclosed includes the possibility to independently adjust the dispense of each of the two materials by acting on the respective dispensing units 3 and 4 through specific triggering signals generated by optional arrangements/devices that can be used in combination with the holding unit 2 to convergingly normalize and prevent fluctuations in the concentration of the liquid composition.

Possible rates for the therapeutic agent may be from 0.03 g/h to 45 g/h. Possible rates for the liquid vehicle may be from 0.6 L/h to 12 L/h. These rates are suitable to target a vast panel of concentrations, notably those that are commonly required for most of pharmaceutical products. For certain applications (excluding compositions including biological therapeutic agents), notably at industrial scale, the rate of the agent may be as high as 36 kg/h. These very high rates are however not preferred for pharmaceutical applications and require adjusting the size of the apparatus units, which is not a desired option.

For example, liquid compositions may be manufactured according to the process presently disclosed by dispensing and feeding a therapeutic agent at a rate of 0.06 g/h or a rate of 9 g/h. Examples of suitable rates for the liquid vehicle may range between 0.6 l/h and 1.2 l/h. The above solid and liquid rates combinations may result in concentrations of 0.1 mg/ml and 7.5 mg/mL.

The dispensing of the therapeutic agent may include microdosing the same. This can be obtained by using a dispensing unit 3 including a microdosing device 8. Microdosing devices are known systems that allow a very precise and accurate continuous or repetitive ("single shot") dispensing of very small amounts of liquid or solid substances. Typically they are capable of dispensing amounts comprised between 0.5 and 20 milligrams (mg), for example lower than 20 mg per 2 seconds or greater time in case of solids. Typically, microdosing devices dispense amounts of a given substance contained as bulk supply in an upstream reservoir.

Examples of suitable microdosing device 8 for solid therapeutic agents are a volumetric vacuum transfer system dispensing device and a stirring system transfer dispensing device. High precision and high accuracy microdosing devices are commercially available e.g. for vial filling, capsule filling, tablet matrix filling.

A stirring system transfer dispensing device is suitable to continuously dispense the therapeutic agent. Continuously feeding and dispensing the therapeutic ingredient may thus include stirring the therapeutic agent within the dispensing unit (3) and continuously pushing the therapeutic agent out of the dispensing unit (3). The pushing out may be proactive or passive (e.g. by gravity).

The dispensing and feeding of the therapeutic agent optionally includes in-line weighing the same e.g. through the use of an agent's moisture content weighing system 9, such as microwave weighing system, or the use of a weight loss weighing system. This option is particularly advantageous when coupled with the use of microdosing.

In-line weighing improves the control on time stability of the predetermined, timely-steady rate because it allows preventing fluctuations in the concentration of the agent. Preventing and normalizing the fluctuations act convergingly to maintain a steady concentration in the final liquid composition.

In-line weighing of the therapeutic agent may include measuring agent's moisture content. In effect, presence of water in the therapeutic agent (e.g. agent's moisture content) may vary over time. In turn, this may modify the amount of agent fed to the mixing unit per time unit and ultimately the therapeutic agent's concentration in the composition. Therefore, in-line weighing of the agent may include in-line taking of microwave spectra of the agent before the latter is admixed with the vehicle, for example before it is fed into the mixing unit 1, such as when the agent is in the conveying elements 5 that fluidly connect the therapeutic agent dispensing unit 3 with the mixing unit 1, and converting these spectra to a mass and water content. Control devices exploiting microwaves, such as a microwave weighing system 9, are commercially available.

The dispensing and feeding of the therapeutic agent and the liquid vehicle may thus include in-line taking of microwave spectra suitable to measure mass and moisture content of the dispensed therapeutic agent, outputting data representing the measured mass and water content dropped, processing the data thereby generating a corresponding signal, and using this signal to dynamically adjust the dispensing and feeding rates of either the therapeutic agent and/or the liquid vehicle. In these manners it is possible to restore the desired qualitative and/or quantitative result (e.g. the target final concentration of the liquid composition) based on which the dispensing and feeding rates were predetermined. For example, the generated signal may be transferred to release actuators operatively connected to the therapeutic agent's and liquid vehicle's dispensing units 3 and 4, in order to keep the ratio between therapeutic agent and liquid vehicle fed to the mixing unit 1 stable over time. The "feedback" control obtained through the in-line weighing further decreases the risk of fluctuations in the safety and quality of the liquid composition.

In-line weighing of the therapeutic agent may include measuring weight loss of the corresponding supply (e.g. the dedicated dispensing unit (3)) during the dispensing of the therapeutic agent. This is particularly advantageous when continuously dispensing the therapeutic agent. Control devices exploiting weight loss are commercially available.

Measuring weight loss may be in addition to, or in alternative to measuring agent's moisture content.

The dispensing and feeding of the therapeutic agent and the liquid vehicle may thus include stirring the therapeutic agent within the dispensing unit (3), continuously dispensing the therapeutic agent from the dispensing unit (3)—e.g. continuously pushing the agent out of the dispensing unit (3)—and measuring weight loss of the dispensing unit (3). Measuring weigh loss may further include outputting data representing the measured mass dropped, processing the data thereby generating a corresponding signal and using this signal to dynamically adjust the dispensing and feeding of either the therapeutic agent and/or the liquid vehicle. For the therapeutic agent, this can be accomplished by adjusting the stirring, e.g. by adjusting stirring speed and/or adjusting the pushing out from the dispensing unit (3). For example, the therapeutic agent may be pushed out through a changeable diameter outlet located for example at the bottom part of the dispensing unit (3) and whose opening size can be modified during the process as a function of data on weight loss.

The mixing may be static or dynamic mixing, preferably dynamic mixing. Devices for performing static or dynamic mixing are known. Particularly suitable are those devices that are already used in the field of fine chemicals. Examples of devices are a mixing device containing a screw (e.g. a screw mixer), a mixing pipe and a mixing vessel. For example, the mixing unit 1 may be a screw mixer. The mixing unit 1 may contain at least a feeding inlet such as at least two feeding inlets 10 and 11, through which the therapeutic agent and the liquid vehicle enter the unit 1, a mixing chamber wherein the therapeutic agent and the liquid vehicle are thoroughly admixed, and an a discharging outlet 12 through which the liquid composition exits the unit 1. In some embodiments, the mixing unit 1 does not contain any mixing effector. In these embodiments, mixing the desired mixing of the agent and the vehicle may be achieved through e.g. turbulent mixing, oscillating flow or static mixing. In other embodiments, like screw mixers, the mixing unit 1 includes a mixing effector, for example a screw, which contributes to the mixing of the therapeutic agent and the vehicle.

Suitable screw mixers may be those commonly used in food or polymer processing. Screw mixers are also used in the field of pharmaceuticals to obtain solid compositions, for example to disperse a solid therapeutic agent with a solid polymer matrix or to granulate powdery excipients. For example, a screw mixer that may be used in the context of the present process is a screw mixer commercialized for hot melt extrusion (HME). Screw mixers of this type are commercially available (for applications other than those envisaged in the present disclosure) from different manufacturers and typically include a barrel containing at least one rotating screw (for example two twin rotating screws) that transports the fed material down the barrel. For example, suitable screw mixers include the following distinct parts:
  a conveying section (mixing chamber), which comprises
    a barrel and at least one rotating screw(s) that transport and mix the fed material, the rotating screw(s) being arranged to rotate along the main longitudinal axis of the barrel;
  a feeding inlet, such as at least two feeding inlets, through which a material (in the present case the therapeutic agent and the liquid vehicle) enters the barrel, and
  a discharging outlet through which the processed material (in this case the liquid composition) exits the screw mixer.

The feeding inlet is typically positioned at a proximal end of the barrel whereas the discharging outlet is positioned at a distal end of the same. Definition of proximal and distal shall be understood with reference to the direction in which the fed material is transported within the barrel by the rotating screw. According to this convention, a proximal end of the barrel is closer to the point in which the material is fed into the barrel whereas a distal end is closer to the point in which the composition leaves the barrel. The screw mixer may include dedicated inlets 10 and 11 for the agent and the vehicle. In this case the agent and the vehicle get in contact only within the mixing unit 1 and the corresponding inlets 10 and 11 are fluidly connected with the therapeutic agent and liquid vehicle supplies, e.g. with the corresponding dedicated dispensing units 3 and 4, through conveying elements 5 and 6. Alternatively, the screw mixer may include one single feeding inlet. In this case, the mixing unit further includes a pre-mixing tank wherein the agent and the liquid get in contact before entering the screw mixer barrel and that is fluidly connected with the feeding inlet through conveying elements.

Once the therapeutic agent and the liquid vehicle are fed to the screw mixer barrel, their homogeneous mixing as well as effective wetting and dissolution of the agent into the vehicle take place in a controllable (i.e. reproducible and repeatable) manner while the therapeutic agent and the liquid vehicle are conveyed down the barrel by means of the at least one rotating screw towards the discharging outlet.

Suitable screw mixers are commercially available for example from Three-Tec GmbH and Thermo Fisher Scientific.

The length and volume of rotating screw are advantageously chosen so as to target a mixing unit residence time (RT) of at least about 5 seconds, for example at least 10 seconds. This mean residence time is regarded as being sufficient to obtain wetting for most combinations of therapeutic agents and liquid vehicles, notably if the latter contains water, when the above rates are adopted. For example, this residence time can be obtained by operating a 12 mm diameter twin screw at 50-250 rpm. If longer residence times are required to obtain appropriate wetting, e.g. because of characteristics of the agent or the vehicle or the use of particularly high rates for agent, the screw length and volume can be progressively increased till reaching the desired result. Adjusting process parameters such as the manner in which the screw is operated (e.g. the rpm of screw rotation), allows modulating the distribution of RT.

In one embodiment the process presently disclosed includes the following steps:
  providing a supply of a therapeutic agent and a liquid vehicle, the supplies being contained in dedicated dispensing units 3 and 4,
  dispensing the therapeutic agent and the liquid vehicle from the corresponding supplies and feeding them into a screw mixer 1 for example by means of conveying elements 5 and 6 fluidly connecting the corresponding dispensing units 3 and 4 and the screw mixer 1, said dispensing and feeding being performed according to a predetermined, timely-steady rate, the rate of the agent and the rate of the liquid vehicle being each independently adjustable (for example through the use of an operatively controlled flowmeter and/or a microdosing device as presently disclosed), the screw mixer 1 including a barrel and at least one screw arranged within the barrel and rotating along a central axis of the latter, at least a feeding inlet 10 and 11 at a proximal end of the barrel and a discharging outlet 12 at a distal, opposite end of the barrel,
  operating the screw so as to mix the agent and the vehicle thereby obtaining a liquid composition while conveying the agent and the vehicle down the barrel towards the discharging outlet 12, said composition having a therapeutic agent concentration,
  discharging the liquid composition from the discharging outlet 12 of the barrel into a holding unit 2, the holding unit 2 being configured so that the unit residence time of the liquid composition is at least sufficient to normalize the therapeutic agent concentration, discharging the liquid composition from the holding unit 2 (e.g. through the use of an operatively controlled flowmeter as presently disclosed) and processing the same.

Like for any other embodiment of the present disclosure, it is possible to combine the use of a screw mixer as mixing unit 1 with a microdosing system 8 and/or an in-line weighing system 9 of the therapeutic agent. Adoption of both microdosing and in-line weighing is preferred.

From the mixing unit 1, the liquid composition is discharged within a holding unit 2. For example, the discharging outlet 12 of a screw mixer is fluidly connected with an inlet 13 of the holding unit 2. Typically, the holding unit 2 is a tank. According to the present disclosure, the holding unit 2 is configured to obtain a residence time of the liquid composition which is at least sufficient to normalize the concentration of the therapeutic agent. This is practically done by configuring the unit so that the liquid composition is retained within the unit for a time suitable to normalize its therapeutic agent concentration.

For a given predetermined dispensing and feeding rate, the concentration of the liquid composition at the exit of the mixing unit might not correspond to a target composition. In other words, when the composition is discharged from the mixing unit 1, its concentration might present fluctuations around a target concentration. This may be associated with process and material parameters such as chosen geometry of the mixing unit 1 (including its mixing mechanism as well as presence, structure and operating parameters of a mixing effector) or phenomena impacting the solubility of the selected therapeutic agent into the selected liquid vehicle such as humidity and temperature of dispensing, feeding and mixing steps.

The present inventors have found that the presence of a holding unit 2 as presently disclosed is a solution to the problem of fluctuations in the concentration of the liquid composition at the exit of the mixing unit 1. Adoption of a holding unit 2 entails the formation of a bulk amount of the liquid composition that, when the holding unit 2 is properly configured, allows normalizing possible negative and positive concentration peaks that are formed in the mixing unit 1 or upstream, e.g. following a non perfect wetting or dissolution of the therapeutic agent. If the liquid composition discharged from the mixing unit 1 were immediately processed for example into single doses (e.g. filled into syringes, cartridges, vials, ampoules or freeze-dried), the risk that one of these doses contain a positive or negative concentration peak would be higher. This risk is reduced and potentially neutralized by the diluting effect brought by the use of holding unit 2.

Accordingly, the liquid composition is retained within the holding unit 2 so as to have a residence time suitable to normalize its concentration. The holding unit can be configured to this purpose by adjusting its volume. Adjusting process parameters such as the position of the inlet 13 through which the liquid composition discharged from the mixing unit 1 enters the holding unit and the position of the outlet 14 through which the composition is discharged from unit 2, allows modulating the distribution of RT.

The process presently disclosed may include further optional steps to optimize the manufacturing of the final liquid pharmaceutical composition.

For example, the process may include a step of discharging the composition from the holding unit 2 and controlling therapeutic agent's concentration in the discharged liquid pharmaceutical composition. Controlling can be effected through conventional means such as non-destructive indirect techniques for example UV and NIR radiation, RAMAN. In case UV, the liquid pharmaceutical composition is inspected using one or more appropriate wave lengths appropriate to quantify the amount of therapeutic agent or/and the amount of excipients in the composition. Control devices 15 exploiting these techniques are commercially available. Controlling therapeutic agent's concentration may include quantifying the agent's concentration in the composition, outputting data representing the measured concentration, processing the data thereby generating a corresponding signal and using this signal to dynamically adjust the dispensing and feeding rates of either the therapeutic agent or the liquid vehicle in order to keep the ratio between therapeutic agent and liquid vehicle fed to the mixing unit 1 stable over time. Adjusting the feeding rate of the liquid vehicle may be done by means of a flowmeter 16 that controls the pump 7. Like for the in-line weighing, this feature achieves an optional "feedback" control on the composition ingredients in order to avoid and promptly correct fluctuations in the target concentration of the therapeutic agent. The controlling step may also include temporarily deviating off-line the liquid pharmaceutical composition discharged from the holding unit 2. Deviating off-line may last for the time necessary to normalize the desired target concentration. Deviating can be accomplished for example by using a three-way flowmeter 17, which controls the pump 24, arranged upstream to the device 15 for controlling therapeutic agent's concentration and downstream to the holding unit.

The process may also include a step of monitoring the pH of the liquid pharmaceutical composition after the latter is discharged from the mixing unit 1. The monitoring can be performed through any commercially available pH monitoring device such as a pH meter 18. Monitoring the pH can also include adjusting the pH of the composition in case this diverges from an intended target pH. In this case the pH monitoring device is an assembly including a pH meter 18 or equivalent device and dedicated reservoirs 19 and 20 containing a supply of a base and/or an acid. The pH monitoring device may be part of (i.e. integrated with) the holding unit 2. The step of monitoring the pH may include measuring the pH of the liquid composition, outputting data representing the measured pH value, processing the data thereby generating a corresponding signal and using this signal to dynamically adjust the pH if need be e.g. by transferring the signal to a release actuator operatively connected to the acid and/or base dedicated reservoirs 19 and 20. In response to the signal, the reservoirs 19 and 20 can release a predetermined amount of said acid and/or base supply and convey it to the liquid composition in order to restore a desired target pH.

The process may also include a step of adjusting the osmolarity of the liquid vehicle that is conveyed from the corresponding reservoir 4 to the mixing unit 1 (i.e. the adjusting may be carried out upstream to the step of feeding the vehicle to the mixing unit 1). The adjusting of the osmolarity can be carried out by adding a predetermined amount of an osmotic agent, for example mannitol or any equivalent agent, to the liquid vehicle before it is fed to the mixing unit 1. A supply of an osmotic agent can be contained in a dedicated reservoir fluidly connected with elements conveying the liquid vehicle from its reservoir to the mixing unit. For example, the elements conveying the liquid vehicle to the mixing unit can include a second reservoir, for example a tank, temporarily stocking the vehicle and wherein a predetermined amount of the osmotic agent can be added. Once the osmotic agent is effectively admixed within the vehicle, the latter is released at a predetermined, timely-steady rate as defined above and conveyed to the mixing unit. Alternatively, the osmotic agent can be added to the liquid vehicle in a continuous way for example by upstream replicating the instant process.

The process may also include a step of filtering the liquid pharmaceutical composition after the latter is discharged from the mixing unit 1, e.g. after discharging the composition from the barrel of a screw mixer (i.e. the filtering may be carried out downstream to the step of discharging and, preferably, also to the step of monitoring the pH). The filtering can be carried out by conveying the liquid pharmaceutical composition through a conventional filter 21 having a desired filtering capacity. The step of filtering may be carried out as last step before filling the liquid pharmaceutical composition final containers for commercialization (e.g. bottles, vials, cartridges, pre-filled syringes, etc.).

In a further aspect, the present disclosure discloses an apparatus for the continuous manufacture of a liquid pharmaceutical composition, for example a continuous manufacture as presently disclosed, the apparatus comprising:

at least two dedicated dispensing units 3 and 4, such as reservoirs, containing a supply of a therapeutic agent and a liquid vehicle, respectively, each dispensing unit 3 and 4 including a release actuator configured to trigger the dispense of the liquid vehicle and the agent at a predetermined, timely-steady rate, the rate of the agent and the rate of the liquid vehicle being each independently adjustable, downstream to the dispensing units 3 and 4, a mixing unit 1 fluidly connected with the dispensing units 3 and 4, the mixing unit 1 including a mixing chamber having proximal and distal ends, a feeding inlet (for example two inlets 10 and 11) at a proximal end of the chamber and a discharging outlet 12 at a distal, opposite end of the chamber, the chamber being configured to receive the therapeutic agent and the liquid vehicle through said inlet, the mixing unit being configured to obtain a liquid composition having a therapeutic agent concentration, downstream to the mixing unit 1, a holding unit 2, e.g. a tank, fluidly connected with the discharging outlet 12 of the mixing unit 1, said holding unit having an inlet 13 and an outlet 14, and said unit 2 being configured to have a residence time of the liquid composition which is at least sufficient to normalize the therapeutic agent concentration, and conveying elements 5, 6 and 22 arranged to fluidly connect the dispensing units 3 and 4 with the feeding inlet of the mixing unit 1 and the discharging outlet 12 of the mixing unit 1 with the inlet 13 of the holding unit 2.

The dispensing unit 4 of the liquid vehicle may be a reservoir, e.g. a tank. The dispensing unit 4 of the liquid vehicle may include a release actuator arranged to trigger the dispense of the liquid vehicle at a predetermined, timely-steady rate, as defined above. This actuator may be a pump and a flow meter.

The dispensing unit 3 of the therapeutic agent may be reservoir, e.g. an agitated hopper. The dispensing unit 3 may include a release actuator arranged to trigger the dispense of the agent at a predetermined, timely-steady rate, as defined above. This actuator may be a microdosing device.

Conveying elements 5 and 6 fluidly connect the dispensing units 3 and 4 of the agent and the vehicle to the mixing unit 1. Conveying elements 6 may further contain a pump 7 or a functionally equivalent component.

The conveying elements 5 connecting the agent's dispensing unit 3 and the mixing unit may include an in-line weighing device 9. For example, in-line weighing device 9 may be configured to in-line taking of microwave spectra of the therapeutic agent and suitable to measure mass and moisture content of the same, outputting data representing the measured mass and water content, processing the data thereby generating a corresponding signal, and using this signal to dynamically adjust the rate at which the release actuators of either the therapeutic agent and/or the liquid vehicle dispense the respective materials. This "feedback" circuit maintains a fix ratio between the amounts of therapeutic agent and the liquid vehicle that are effectively fed to the mixing unit 1 over time. The in-line monitoring device 9 may be a microwave weighing device, configured so as to in-line monitor mass and moisture content of the therapeutic agent and output data representing the measured values. The in-line monitoring device 9 may also include a processor that may be operatively connected with the dispensing units 3 and 4 of the therapeutic agent and/or the liquid vehicle. For example, the processor may be configured to receive the data from the weighing device 9, process the same and output a signal to the release actuators thereby dynamically adjusting the therapeutic agent and/or liquid vehicle dispensing and feeding manner.

The mixing unit 1 is configured to obtain a liquid composition having a therapeutic agent concentration. Any suitable known mixing unit can be used. In a preferred embodiment, the mixing unit 1 may be a screw mixer including a rotating screw, as disclosed above. The use of a screw mixer as mixing unit in the context of a process for the continuous manufacture of a liquid pharmaceutical composition was unknown.

With reference to the disclosure of a screw mixer made above, the screw mixer's barrel may include a feeding inlet (e.g. an opening) dedicated to feeding the therapeutic agent and a distinct feeding inlet (e.g. an opening) dedicated to feeding the liquid vehicle. Both inlets 10 and 11 may be positioned at a distal end of the barrel. In one embodiment, the feeding inlet 10 dedicated to the feeding of the therapeutic agent is positioned on the barrel downstream to the feeding inlet 11 dedicated to the vehicle. Unless otherwise indicated, downstream and upstream shall be understood to be expressed with respect to the direction in which material (i.e. the therapeutic agent, the vehicle and the corresponding pharmaceutical composition) flows in the apparatus.

The holding unit 2 is configured to obtain a residence time of the liquid composition which is at least sufficient to normalize the therapeutic agent concentration. This is done by retaining the liquid composition within the holding unit 2 for a time suitable to normalize that concentration. The presence of a holding unit 2 thus counterbalances the negative impact on final product's safety and efficacy that possible fluctuations in the concentration of the therapeutic agent at the exit of the mixing unit 1 may have. Possible manners to configure the holding unit 2 to obtain this result are disclosed above. For example, the geometry of the unit 2, e.g. its volume or the mutual positions of its inlet 13 and outlet 14, can be adjusted in order to modify the liquid composition mean residence time and its distribution, respectively, till achieving the desired effect. Longer-than-necessary holding unit residence times may be adopted but are less preferred. Once the normalization objective has been achieved, longer resides times (due e.g. to oversized holding units) do not bring any appreciable advantage while increasing overall process residence time (which entails longer running times and higher costs, which are typically undesirable factors).

The various elements/devices/units of the instant apparatus are fluidly connected as appropriate by means of conveying elements (e.g. 5, 6 and 22) that convey the material (e.g. the therapeutic agent, the liquid vehicle and the liquid pharmaceutical composition) from the reservoirs 3 and 4 to the mixing unit 1 and then away from that unit 1 into the holding unit 2.

Other conveying elements 23 may be present to convey the liquid pharmaceutical composition away from the holding unit 2 towards further processing units such as a filtration, filling or primary packaging machine or a freeze-drying station.

The apparatus presently disclosed may further include optional devices or arrangements that can be positioned downstream or upstream to the mixing unit 1 in order to carry out steps that optimize the characteristics of the pharmaceutical composition, e.g. to convergingly act with the holding unit 2 and the in-line weighing device 9, to avoid fluctuations in the concentration of the liquid composition.

The elements 23 that convey the liquid composition away from the holding unit 2 may include a concentration control arrangement 15 arranged to control therapeutic agent's concentration in the liquid pharmaceutical composition. For example, this arrangement 15 includes a device relying on UV, NIR or RAMAN spectroscopy. Technique of characterize a liquid composition through e.g. UV absorbance by the solute (in this case, the therapeutic agent) or NIR or RAMAN spectroscopy are known in the field of pharmaceuticals and commercially available. The concentration control arrangement 15 may be configured to quantify the therapeutic agent in the composition e.g. through the absorbance at a API-specific waves lengths, output data that represents the measured API/excipient concentration and process the data thereby generating a corresponding signal. This signal can be transferred through appropriate elements to the release actuators of dispensing units 3 and 4 of either the therapeutic agent and/or the liquid vehicle in order to adjust the dispensing and feeding rates and ultimately normalize the concentration of the agent in the pharmaceutical composition. Implementing a control arrangement such as the one presently disclosed allows obtaining a real time quality control.

The conveying elements 6 that convey the liquid vehicle from its dispensing unit 4 to the mixing unit 1 may also include a liquid vehicle feeding control device 16 and 7, e.g. a flowmeter. This device may be operatively connected to, and actuated by either one of the signals generated by the in-line weighing device 9 and the concentration control arrangement 15. By realizing a "feedback" dynamic adjustment of the feeding of the liquid vehicle, the present apparatus provides for a further mechanism to avoid or normalize fluctuations in the therapeutic agent concentration.

The elements 23 that convey the liquid composition away from the holding unit 2 may further include a pump 24 or a functionally equivalent component. The elements 23 that convey the liquid composition away from the holding unit 2 may further include a second flowmeter 17 or functionally equivalent device. This second flowmeter 17 may be operatively connected to the concentration control arrangement 15 and may be operated to temporarily deviate off-line the liquid pharmaceutical composition discharged from the holding unit 2 in case of severe, non-corrected fluctuations of the agent's concentration. The second flowmeter 17 may be operated for the time necessary to restore the intended API concentration. The second flowmeter 17 that controls the pump 24 may be in the form of a three-way valve when it is desired to deviate the liquid composition off-line, as disclosed above.

For example, the holding unit 2 may include an arrangement to monitor the pH of the liquid pharmaceutical composition and optionally correct the same in case of divergences with respect to a predetermined target pH. The arrangement may include a device to monitor the pH, such as any commercially available pH meter 18, a reservoir 20 containing a supply of a base and/or a reservoir 19 containing a supply of an acid, the reservoirs 19 and 20 being fluidly connected to the pH monitoring device 18, and conveying elements 25 connecting the arrangement to the holding unit 2. Predetermined amounts of base and/or acid can be released from the reservoirs 19 and 20 according to a signal generated by the pH measuring device 18. These amounts are then added to the liquid pharmaceutical composition into the holding unit 2 through conveying element 25 by the pumps 26 and 27 to restore the predetermined pH value.

The apparatus may further include dedicated arrangements to add further excipients for the composition, such as excipients to adjust the osmolarity the liquid pharmaceutical composition as disclosed above.

Downstream to the holding unit 2, the apparatus may further include an arrangement 21 to filter the liquid pharmaceutical composition. Preferably, the arrangement—that may include a conventional filter for pharmaceutical purposes and whose filtering capacity can be chosen depending in the intended use—is arranged so as to be the last downstream element before the composition is finally processed e.g. filled, into vials or syringes or freeze-dried. Therefore, the filtering arrangement 21 may be positioned downstream to both the holding unit 2 and the concentration control arrangement 15.

The apparatus may also include an arrangement to freeze-dry the liquid composition and therefore transform it into a solid one.

The apparatus may also include an arrangement to collect the finished composition in bulk and/or divide it into single dosage form units (e.g. vials or syringes or freeze-dried doses) for mono- or multidose packaging.

In a further aspect the present disclosure discloses the use of an assembly including
 a microdosing device 8,
 downstream to the microdosing device 8, an in-line weighing device 9, and
 downstream to the in-line weighing device 9, a holding unit 2,
each being for example as presently disclosed, for maintaining a steady concentration of a therapeutic agent during a continuous manufacturing of a liquid pharmaceutical composition, the composition containing said agent and a liquid vehicle.

Maintaining a steady concentration means preventing and/or normalizing fluctuations (i.e. positive and/or negative peaks) in the therapeutic agent concentration of the composition.

The assembly may also include a mixing unit 1 positioned downstream to the in-line weighing 9 device and upstream to the holding unit 2. This mixing unit 1 may be a screw mixer as presently disclosed.

The assembly may further include dispensing units 3 and 4 arranged to dispense a supply of the therapeutic agent and a supply of the liquid vehicle, and a concentration control arrangement 15, arranged to control therapeutic agent's concentration in the pharmaceutical composition, and operatively connected with said dispensing elements 3 and 4. In this embodiment, a "feedback" circuit is thus realized that contributes in a converging manner with the rest of the assembly to promptly spot fluctuations in the concentration of the therapeutic agent in the composition and trigger a corresponding counter-adjustment of the therapeutic agent and/or liquid vehicle dispensing.

In a further aspect the present disclosure discloses an assembly including:
- a microdosing device 8,
- downstream to the microdosing device 8, an in-line weighing device 9, and
- downstream to the in-line weighing device 9, a holding unit 2, each being for example as presently disclosed, configured for maintaining a steady concentration of a therapeutic agent during a continuous manufacturing of a liquid pharmaceutical composition, the composition containing said agent and a liquid vehicle.

The various aspects presently disclosed make it possible a continuous, preferably automated, manufacture of a liquid pharmaceutical composition including a therapeutic agent, notably a biotechnological active ingredient. The process and the apparatus can be readily scaled-up/down by simply adjusting the run time or flow rates in order to fit a broad array of different manufacturing needs. The aspects presently disclosed can be swiftly adapted to development, investigational and commercial scale productions. This is possible inter alia due to short development time, the possibility to work with low amounts of therapeutic agent, overall small footprint, reduced waste production and presence of solutions to maintain a tight control on key composition parameters such as the therapeutic agent concentration in the liquid composition. Automation can also be achieved so as to make the process and the apparatus compliant with most recent requirements in terms of quality and safety for pharmaceuticals manufacturing.

Further embodiments and advantages of the aspects presently disclosed will become apparent to a skilled reader in light of the examples provided below.

Examples

An amorphous peptide API, was added to 12 mm diameter and 240 mm length screw mixer using microdosing at a frequency of about 5 mg doses every 45 s. A liquid vehicle, containing water for injection and excipients at a concentration of about 5% was added at rate of about 65 ml/min. The mixer screw was turned at 200 rpm and the solution was led into a tank with a liquid volume of about 100 ml. The solution was stirred and the pH was continuously adjusted to 4.5 using 10% HCl or 10% NaOH solution. An outlet pump was connected to the tank and the solution output flow was set to about 65 ml/min in order to keep the tank volume constant at about 100 ml. The solution was pumped through a 0.45 µm and 0.2 µm combined filter and the API concentration was measured on-line using a UV method. The concentration was found to reach steady state in 12 minutes, after which a concentration of 0.1 mg/ml+/−5% was held for about 1 h 30 min before ending the experiment.

An amorphous peptide API, was added to 12 mm diameter and 240 mm length screw mixer using microdosing at a frequency of about 5 mg doses every 2.4 s. A liquid vehicle, containing water for injection and excipients at a concentration of about 5% was added at rate of about 17 ml/min. The mixer screw was turned at 200 rpm and the solution was led into a tank with a liquid volume of about 25 ml. The solution was stirred and the pH was continuously adjusted to 4.5 using 10% HCl or 10% NaOH solution. An outlet pump was connected to the tank and the solution output flow was set to about 17 ml/min in order to keep the tank volume constant at about 27 ml. The solution was pumped through a 0.45 µm and 0.2µ combined filter and the API concentration was measured on-line using a UV method. The concentration was found to reach steady state in 9 minutes, after which a concentration of 7.5 mg/ml+/−3% was held for about 1 h before ending the experiment.

The invention claimed is:

1. An apparatus for the continuous manufacture of a liquid pharmaceutical composition, comprising:
   at least two dedicated dispensers configured to contain a supply of a therapeutic agent and a liquid vehicle, respectively, wherein each dispenser comprises a release actuator, wherein the release actuator of the dispenser configured to contain the liquid vehicle is configured to trigger dispensing of the liquid vehicle at a predetermined, time-steady rate and the release actuator of the dispenser configured to contain the therapeutic agent is configured to trigger dispensing of the therapeutic agent at a predetermined, time-steady rate, wherein each of the rate at which the therapeutic agent is dispensed and the rate at which the liquid vehicle is dispensed is independently adjustable;
   a mixer downstream of the dispensers, wherein the mixer is fluidly connected with the dispensers and comprises a mixing chamber having proximal and distal ends, a feeding inlet at a proximal end of the mixing chamber and a discharging outlet at a distal, opposite end of the mixing chamber, wherein the chamber is configured to receive the therapeutic agent and the liquid vehicle through said inlet, wherein the mixer is configured to obtain a liquid composition having a concentration of the therapeutic agent;
   a holder downstream of the mixer, wherein the holder is fluidly connected with the discharging outlet of the mixer and comprises an inlet and an outlet and is configured to hold the liquid composition for a residence time that is at least sufficient to normalize the concentration of the therapeutic agent, and
   conveyors arranged to fluidly connect the dispensers with the feeding inlet of the mixer, and to fluidly connect the discharging outlet of the mixer with the inlet of the holder, wherein the conveyors connecting the dispenser configured to contain the therapeutic agent and the mixer comprise an in-line microwave weigher including a processor,
   wherein the in-line microwave weigher including the processor is configured to (i) perform in-line taking of microwave spectra of the therapeutic agent suitable to measure mass and moisture content of the therapeutic agent, (ii) output data representing the measured mass and moisture content, (iii) process the data to generate a corresponding signal, and (iv) provide the signal to the dispensers to permit dynamic adjustment of the rate at which the release actuators of one or both of the therapeutic agent and the liquid vehicle dispense the respective materials from the dispensers.

2. The apparatus according to claim 1, wherein mixer is a screw mixer.

3. The apparatus according to claim 1, wherein the in-line microwave weigher is configured to measure weight loss of the therapeutic agent dispenser.

4. The apparatus according to claim 1, further comprising a controller configured to perform UV, NIR or RAMAN spectrometry of the therapeutic agent.

5. The apparatus according to claim 1, wherein the holder further comprises a pH monitor configured to monitor pH of the liquid composition and optionally configured to correct the pH of the liquid composition in case of divergence from a predetermined target pH.

* * * * *